United States Patent [19]
Brown et al.

[11] 4,263,807
[45] Apr. 28, 1981

[54] GUN BARREL STRESS SIMULATOR

[75] Inventors: Bruce B. Brown, Schenectady; Joesph Wido; George Sogoian, both of Latham, all of N.Y.

[73] Assignee: The United States of America as represented by the Secretary of the Army, Washington, D.C.

[21] Appl. No.: 72,278

[22] Filed: Sep. 4, 1979

[51] Int. Cl.³ .............................................. G01L 5/14
[52] U.S. Cl. ..................................................... 73/167
[58] Field of Search .................. 73/167, 816, 432 SD, 73/46, 49.8; 277/27, 34.3

[56] References Cited

U.S. PATENT DOCUMENTS 3,693,432  9/1972  Stewart .................................. 73/167
3,919,880  11/1975  Seyd et al. ............................ 73/49.8

FOREIGN PATENT DOCUMENTS 1048568  2/1979  Canada ..................................... 277/27

Primary Examiner—Jerry W. Myracle
Attorney, Agent, or Firm—Nathan Edelberg; Robert P. Gibson; A. Victor Erkkila

[57] ABSTRACT

A simulator has a barrel arranged to launch a projectile. The simulator includes a stress device for stressing the barrel. This stress device comprises a piston slidably mounted within the barrel. This piston is operative to expand at its periphery. Also included in the stress device is a seal that is sealed to the barrel and is spaced alongside the piston. The piston is positioned between the seal and the muzzle of the barrel. Pressurized fluid can be applied to the above equipment to pressurize the interspace between the piston and the seal.

8 Claims, 2 Drawing Figures

GUN BARREL STRESS SIMULATOR

GOVERNMENTAL INTEREST

The invention described herein may be manufactured, used and licensed by or for the government for governmental purposes without the payment to us of any royalties thereon.

BACKGROUND OF THE INVENTION

The present invention relates to simulators and in particular to arrangements for simulating the stress applied to a barrel by a projectile and by gun gas.

It is desirable to simulate the stress caused by the firing of a projectile through a barrel in order to measure the resulting strain. In addition, it is desirable to repeatedly simulate such stress so that barrel fatigue can be assessed. There are two general causes of stress during the firing of a projectile. Firstly, there is the stress caused by the gun gas. Secondly, there is the stress caused by the obturator of the projectile. This obturator, being larger than the bore of the barrel, is designed to deformably engage the rifling of a barrel.

The disadvantages surrounding firing an actual projectile merely for test purposes is evident. The projectile must either be fired into a large restraining target or into a large firing range. For repeated firings the cost can be exceedingly high. Merely pressurizing the barrel does not accurately simulate the stresses occurring during firing since this provides uniform stress as opposed to the non-uniform stress that actually occurs.

The present invention provides a simple and effective method for simulating the complex stresses caused by the firing of a projectile. A simple stress test is provided by employing a piston having an expansible periphery. The periphery of this piston is expanded and the barrel is pressurized between its breech and the piston to simulate the complex stresses produced by the firing of a projectile.

SUMMARY OF THE INVENTION

In accordance with the illustrative embodiments demonstrating features and advantages of the present invention there is provided in a simulator, a stress means. This simulator has a barrel which is arranged to launch a projectile. The stress means includes a piston means, a seal means and a pressure means. The piston means is slidably mounted within the barrel. This piston is operative to expand at its periphery. The seal means is sealed to the barrel and is spaced alongside the piston means. The piston means is positioned between the seal means and the muzzle of the barrel. The pressure means is operative to pressurize the interspace between the piston means and the seal means.

An associated method is provided for testing a barrel having a sealed breech with a piston. The piston has an expansible annulus in an annular groove. The piston also has a port communicating with the annular groove. The method includes the step of positioning the piston within the barrel. The method also includes the step of applying pressurized fluid to the port to expand the annulus to an extent sufficient to simulate stress applied to the barrel by a projecile. The method also includes the step of applying pressurized fluid at a location between the piston and the breech of the barrel. This pressurization occurs to an extent sufficient to simulate the pressure produced by gun gas.

BRIEF DESCRIPTION OF THE DRAWINGS

The above brief description as well as further objects, features and advantages of the present invention will be more fully appreciated by reference to the following detailed description of a presently preferred but nonetheless illustrative embodiment in accordance with the present invention when taken in conjunction with the accompanying drawings wherein.

DETAILED DESCRIPTION OF THE PREFERRED EMBODIMENT

Figure 1:
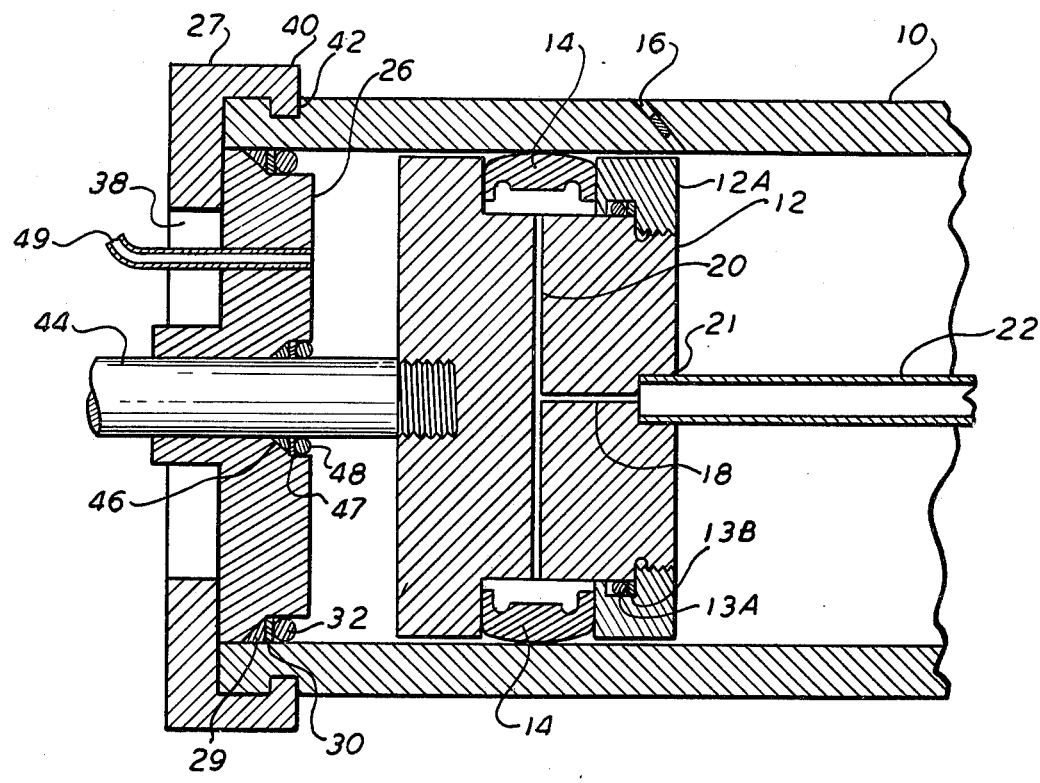
FIG. 1 is a sectional view of a simulator in accordance with the present invention.

Referring now specifically to the drawings, in FIG. 1 there is shown a simulator having a barrel 10, which is an elongated hollow cylinder. Barrel 10 is shown broken on its right end for illustrative purposes. While barrel 10 is shown having a smooth bore, some embodiments may employ rifling.

Mounted within barrel 10 is a piston means, shown herein as driven member 12 and expansible annulus 14. Piston 12, which includes threaded annular segment 12A, is essentially a cylinder having a rectangular groove cut into its outer periphery. Toroidal rubber gasket 13A and flat leather washer 13B seal segment 12A. Annulus 14 is an axially symmetric seal having the illustrated cross section. Annulus 14 is composed of metal having a yield strength sufficiently high so that it does not extrude into apertures or cracks on the inside surface of barrel 10. Such as aperture is shown herein as plugged vent 16. If unplugged and coupled to a known plenun, vent 16 would provide a draft to clear smoke from the barrel. Annulus 14 is sized to intimately contact the inside surface of barrel 10. In the event barrel 10 is rifled, annulus 14 will have a matching periphery. Annulus 14 is somewhat elastic and can expand slightly in response to pressure applied to its inside surface. While the outside surface of annulus 14 is shown curved, the specific geometry employed will be chosen to simulate the geometry of a specific rotating band obturator of a projectile. Piston 12 also has a network of passages comprising coaxial bore 18 and radial bore 20. These bores communicate between port 21 and the interspace between annulus 14 and piston 12. A source of hydraulic pressure is coupled through pipe 22 to port 21. While the piston means is shown herein as piston 12 and expansible annulus 14, it is to be understood that other arrangements are possible. For example, a cone may be mechanically wedged into a cavity of piston 12 to outwardly propel a plurality of radial members which, in turn, bear upon annulus 14.

A seal means is shown herein as an annular closure comprising coaxial disc 26 and retaining ring 27. The periphery of disc 26 is circular and sized to engage and seal to the inside surface of barrel 10. Such sealing is facilitated by triple gaskets comprising wedge-shaped, aluminum gasket 29, flat leather gasket 30 and toroidal rubber gasket 32. Retaining ring 27 is shown herein as an annular plate having a relatively large concentric aperture 38 and an L-shaped shoulder 40 which engages matching annular groove 42 in barrel 10. It is to be understood that for practical reasons, ring 27 is constructed as a split ring which is suitably fastened together.

An elongated member is shown herein as connecting rod 44 which is threaded into piston 12. Rod 44 extends through a concentric aperture in disc 26 and is sealed thereto by gaskets 46, 47 and 48. Gaskets 46, 47 and 48 are shaped and composed similarly to gaskets 29, 30 and 32, respectively. While rod 44 is arranged to slide through disc 26, other arrangements are anticipated. For example, some embodiments may employ a seal means which consists of a rod and disc, similar to rod 44 and disc 26, except that they are rigidly attached. Alternatively, instead of rod 44, another rod may be employed which has a thickened aft end which is sized to seal to the barrel.

Figure 2:
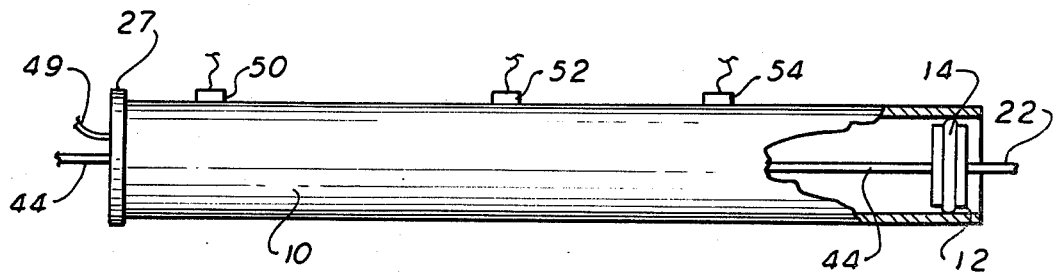
FIG. 2 is an elevational view of the apparatus of FIG. 1.

Referring now to FIG. 2, barrel 10, previously illustrated in part, is shown in full length but with a portion of its right end broken away, for illustrative purposes. It will be observed that connecting rod 44 and piston 12 are coaxially mounted within barrel 10, but are shown positioned near the muzzle of barrel 10. Mounted on the outside surface of barrel 10 are a plurality of strain gauges 50, 52 and 54. These strain gauges are shown with broken electrical wires projecting from them.

In order to facilitate an understanding of the present invention, the operation of the foregoing embodiment will be briefly described. With piston 12 positioned as illustrated in FIG. 1, hydraulic pressure is initially applied through line 22. This pressure, communicated through bores 18 and 20, apply an outward pressure to the inside face of annulus 14. In response, annulus 14 expands and bears against the inside surface of barrel 10. The amount of pressure applied to annulus 14 is chosen to cause a stress upon barrel 10 sufficient to simulate the stress caused by the obturator of a projectile. Hydraulic pressure is now fed through line 49 to pressurize the interspace between disc 26 and piston 12.

In this condition a nonuniform radial stress is applied to the inside surface of barrel 10. Connecting rod 44 controls the movement of piston 12 down barrel 10 such that the pressure in the interspace between disc 26 and piston 12 can be stabilized or varied relative to piston travel. As piston 12 moves along barrel 10 and encounters nonuniformities such as bore 16, complex strain patterns are produced. In this fashion, these mechanical variations are detected along the length of barrel 10 by means of strain gauges 50, 52 and 54 (FIG. 2). When connecting rod 44 has reached the desired extent of travel, piston 12 is in the position shown in FIG. 2. At this time pressure may be removed from lines 49 and 22. Connecting rod 44 is now withdrawn from barrel 10 thereby retracting piston 12. Accordingly, piston 12 moves back toward disc 26. When connecting rod 44 is fully withdrawn, piston 12 returns to the position shown in FIG. 1. This completes one cycle and the apparatus is prepared to undertake another cycle.

The foregoing events may occur at a relatively rapid rate so that the rapid movement of a projectile can be simulated. Also the foregoing cycle can be repeated at a high rate to quickly determine the fatigue and wear charcteristics of barrel 10.

It is appreciated that numerous modifications can be implemented with respect to the apparatus and equipment described above. For example, piston 12, rod 44 and disc 26 can employ different shapes. In addition, gaseous pressure may be substituted for liquid pressure in some embodiments. Also, various materials may be employed to provide the desired strength, weight, wear, etc. Obviously many other modifications and variations of the present invention are possible in light of the above teachings. It is therefore to be understood that within the scope of the appended claims, the invention may be practiced otherwise than specifically described.

We claim:

1. In a simulator having a barrel arranged to launch a projectile a stress means comprising:
   a piston means slidably mounted within said barrel, said piston means comprising a driven member having on its periphery an annular groove, said driven member having a port on a side opposite the breech of said barrel, said port internally communicating with said groove, and an expansible annulus mounted within said groove; whereby sufficient pressure applied to said port causes a radially outward force to be applied to said barrel by said annulus,
   seal means sealed to said barrel and spaced alongside said piston means, said piston means being positioned between said seal means and the muzzle of said barrel;
   pressure means for pressurizing the interspace between said piston means and said seal means, and
   strain gauge means for detecting mechanical variations along the length of said barrel.

2. In a simulator according to claim 1 further including:
   an elongated member coaxially mounted on said piston means for restraining its movement.

3. In a simulator according to claim 2 wherein said elongated member extends out of the breech of said barrel and wherein said seal means comprises:
   an annular closure sealed to said breech and said elongated member, said elongated member being slidable through said annular closure.

4. In a simulator according to claim 3 wherein said annular closure has an aperture, said pressure means applying high pressure fluid through said aperture.

5. In a simulator according to claim 1 or 2 wherein said seal means comprises:
   a coaxial disc fixedly attached to said elongated member at a predetermined distance from said piston means.

6. In a simulator according to claim 2 wherein said seal means comprises:
   a disc having a concentric and eccentric aperture mounted within and sealed to said barrel; said elongated member being slidably mounted in and sealed to said concentric aperture, said pressure means being applied through said eccentric aperture; and
   a retaining ring mounted on the breech of said barrel and sized to prevent said disc from being discharged from said breech.

7. A method for testing a barrel having a sealed breech with a piston having an expansible annulus in an annular groove, said piston having a port communicating with said annular groove, comprising the steps of:
   positioning said piston within said barrel;
   applying pressurized fluid to said port to expand said annulus to an extent sufficient to simulate the stress applied to said barrel by a projectile; and
   applying pressurized fluid at a location between said piston and the breech of said barrel to an extent sufficient to simulate the pressure produced by gun gas.

8. A method according to claim 7 wherein said piston has attached to it an elongated member that projects through said breech, said method further including the steps of:
   moving said elongated member and said piston through said barrel, whereby motion of a projectile through said barrel is simulated.

* * * * *